US00PP32329P2

(12) United States Plant Patent

Gomez Bullis

(10) Patent No.: US PP32,329 P2
(45) Date of Patent: Oct. 13, 2020

(54) *AECHMEA* PLANT NAMED 'PINK TANGO'

(50) Latin Name: ***Aechmea dichlamydea var. dichlamydea* X *(Aechmea tessmanii* X *Aechmea fasciata)***
Varietal Denomination: Pink Tango

(71) Applicant: Patricia E. Gomez Bullis, Princeton, FL (US)

(72) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 0 days.

(21) Appl. No.: 16/602,185

(22) Filed: Aug. 23, 2019

(51) Int. Cl.
*A01H 5/12* (2018.01)
*A01H 6/22* (2018.01)

(52) U.S. Cl.
USPC ..... Plt./370
CPC ..... *A01H 6/223* (2018.05)

(58) Field of Classification Search
USPC ..... Plt./370
CPC ..... A01H 6/223; A01H 6/22
See application file for complete search history.

*Primary Examiner* — Anne Marie Grunberg
(74) *Attorney, Agent, or Firm* — C. A. Whealy

(57) ABSTRACT

A new and distinct cultivar of *Aechmea* plant named 'Pink Tango', characterized by its upright and to slightly outwardly arching growth habit; large light green-colored leaves with dense trichomes giving a silvery appearance; freely-flowering inflorescences held upright and above the foliar plane on straight strong red purple-colored scapes; compact, dense and branched inflorescences with red purple-colored flower and scape bracts; and long-lasting inflorescences.

2 Drawing Sheets

Botanical designation: *Aechmea dichlamydea* var. *dichlamydea* X (*Aechmea tessmanii* X *Aechmea fasciata*).
Cultivar denomination: 'PINK TANGO'.

BACKGROUND OF THE INVENTION

The present invention relates to a new and distinct *Aechmea* plant, botanically known as *Aechmea dichlamydea* var. *dichlamydea* X (*Aechmea tessmanii* X *Aechmea fasciata*) and hereinafter referred to by the cultivar name 'Pink Tango'.

The new *Aechmea* plant is a product of a planned breeding program conducted by the Inventor in Princeton, Fla. The objective of the breeding program was to create new *Aechmea* plants with unique foliage and inflorescence coloration and good postproduction longevity.

The new *Aechmea* plant originated from a cross-pollination made by the Inventor in 2005 in Princeton, Fla., of an unnamed selection of *Aechmea dichlamydea* var. *dichlamydea*, not patented, as the female, or seed, parent with an unnamed selection of *Aechmea tessmanii* x *Aechmea fasciata*, not patented, as the male, or pollen, parent. The new *Aechmea* plant was discovered and selected by the Inventor as a single flowering plant from within the progeny of the stated cross-pollination in a controlled greenhouse environment in Princeton, Fla. in 2005.

Asexual reproduction of the new *Aechmea* plant by offsets in a controlled greenhouse environment in Princeton, Fla. since 2006 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pink Tango'. These characteristics in combination distinguish 'Pink Tango' as a new and distinct *Aechmea* plant:

1. Upright and to slightly outwardly arching growth habit.
2. Large light green-colored leaves with dense trichomes giving a silvery appearance.
3. Freely-flowering inflorescences held upright and above the foliar plane on straight strong red purple-colored scapes.
4. Compact, dense and branched inflorescences with red purple-colored flower and scape bracts.
5. Long-lasting inflorescences.

Plants of the new *Aechmea* differ from plants of the female parent selection primarily in the following characteristics:

1. Leaves of plants of the new *Aechmea* are light silvery green in color whereas leaves of plants of the female parent selection are darker green in color.
2. Inflorescences of plants of the new *Aechmea* are more compact and denser than inflorescences of plants of the female parent selection.
3. Inflorescences of plants of the new *Aechmea* are upright whereas inflorescences of plants of the female parent selection are recurved.
4. Inflorescences of plants of the new *Aechmea* are red purple in color whereas inflorescences of plants of the female parent selection are pale bluish green in color.

Plants of the new *Aechmea* differ from plants of the male parent selection primarily in the following characteristics:

1. Leaves of plants of the new *Aechmea* are light silvery green in color whereas leaves of plants of the male parent selection are pink in color.
2. Leaves of plants of the new *Aechmea* are upright to slightly outwardly arching whereas leaves of plants of the male parent selection are outwardly arching.
3. Plants of the new *Aechmea* have taller inflorescences than plants of the male parent selection.
4. Inflorescences of plants of the new *Aechmea* are red purple in color whereas inflorescences of plants of the male parent selection are pink and yellow in color.

Plants of the new *Aechmea* can be compared to plants of *Aechmea dichlamydea trinitensis* X *Aechmea fendleri* 'Blue Tango', disclosed in U.S. Plant Pat. No. 11,743. In side-by-side comparisons, plants of the new *Aechmea* and 'Blue Tango' differ primarily in the following characteristics:

1. Leaves of plants of the new *Aechmea* are more upright than and not as arching as leaves of plants of 'Blue Tango'.
2. Leaves of plants of the new *Aechmea* are light silvery green in color whereas leaves of plants of 'Blue Tango' are more glaucous and darker green in color.
3. Inflorescences of plants of the new *Aechmea* are red purple in color whereas inflorescences of plants of 'Blue Tango' are bluish purple and fuchsia red in color.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color vallies cited in the detailed botanical description which accurately describe the colors of the new *Aechmea* plant.

The photograph on the first sheet is a side perspective view of a typical flowering plant of 'Pink Tango' grown in a container.

The photograph on the second sheet is a close-up view of a typical flowering plant of 'Pink Tango'.

DETAILED BOTANICAL DESCRIPTION

The aforementioned photographs and following observations, measurements and values describe plants grown in 20-cm containers during the spring and early summer in a polypropylene-covered shadehouse in Princeton, Fla. During the production of the plants, day temperatures ranged from 18° to 30° C., night temperatures ranged from 16° C. to 28° C. and light levels ranged from 2,800 to 3,200 foot-candles. Plants were 15 months old when the photographs and description were taken. In the following description, color references are made to The Royal Horticultural Society Colour Chart, 2015 Edition, except where general terms of ordinary dictionary significance are used.

Botanical classification: *Aechmea dichlamydea* var. *dichlamydea* X (*Aechmea tessmannii* x *Aechmea fasciata*) 'Pink Tango'.

Parentage:

*Female, or seed, parent.*—Unnamed selection of *Aechmea dichlamydea* var. *dichlamydea.*

*Male, or pollen, parent.*—Unnamed selection of *Aechmea tessmannii* x *Aechmea fasciata.*

Propagation:

*Type.*—By offsets.

*Time to initiate roots, summer.*—About 30 to 45 days at temperatures ranging from 28° C. to 30° C.

*Time to initiate roots, winter.*—About 60 to 90 days at temperatures ranging from 18° C. to 20° C.

*Time to produce a rooted young plant, summer.*—About four months at temperatures ranging from 28° C. to 30° C.

*Time to produce a rooted young plant, winter.*—About five months at temperatures ranging from 18° C. to 20° C.

*Root description.*—Fine, fibrous; typically beige to brown in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and to slightly outwardly arching growth habit; rosette leaves are erect when young, becoming slightly outwardly arching with development; plants readily produce offsets; vigorous growth habit.

*Plant height, soil surface to top of leaf canopy.*—About 74 cm.

*Plant height, soil surface to top of inflorescence.*—About 101 cm.

*Plant diameter or spread.*—About 78 cm.

Leaf description:

*Arrangement.*—Rosette, spiral phyllotaxis; leaves clasping; simple.

*Length.*—About 68 cm.

*Width, flattened.*—Distally, about 5 cm; at the base, about 11 cm.

*Shape.*—Lanceolate, strap-like.

*Apex.*—Sharply cuspidate.

*Base.*—Truncate.

*Margin.*—Pectinate; sharply spinose.

*Aspect.*—Upright to slightly arching with development.

*Texture and luster, upper and lower surfaces.*—Smooth, glabrous; leathery; stiff; densely covered with trichomes; slightly glossy.

*Venation.*—Parallel.

*Color.*—Developing and fully expanded leaves, upper surface, after removing trichomes: Close to 144A; venation, close to 144A; trichomes, close to NN155D. Developing and fully expanded leaves, lower surface, after removing trichomes: Close to 144A; venation, close to 144A; trichomes, close to NN155D.

*Marginal spines.*—Density: About three to four per cm. Length: About 2.5 mm. Diameter: Less than 1 mm. Shape: Acicular with sharp apices. Texture and luster: Smooth, glabrous; glossy. Color: Close to 187A.

Inflorescence description:

*Inflorescence form and arrangement.*—Long, open terminal panicles with tightly branched lateral panicles supported by erect and strong scapes; about 24 lateral panicles each with about 15 to 17 individual flowers; flowers distichous, sessile.

*Time to flower.*—Plants begin flowering about 11 to 13 weeks after planting.

*Inflorescence longevity.*—Inflorescences of the new *Aechmea* are very long-lasting, typically bract color will be maintained for about two months in the interior and about 2.5 to 5 months in the interior landscape depending on environmental conditions; flowers and inflorescences persistent.

*Fragrance.*—None detected.

*Inflorescence length.*—About 37.5 cm.

*Inflorescence width.*—About 23 cm.

*Lateral inflorescence length.*—About 9 cm.

*Lateral inflorescence width.*—About 2.75 cm.

*Flower buds.*—Length: About 1.5 cm. Diameter: About 5 mm. Shape: Ovoid, pointed. Texture and luster: Smooth, glabrous; glossy. Color: Close to N57A.

*Flower length.*—About 2.5 cm.

*Flower diameter.*—About 7.5 mm.

*Petals.*—Quantity and arrangement: Three in a single whorl. Length: About 2 cm. Width, proximally: About 5 mm. Shape: Elongated ovate to lanceolate. Apex: Acute. Base: Truncate. Margin: Entire. Texture and luster, inner and outer surfaces: Smooth, glabrous, waxy; glossy. Color: When opening and fully opened, inner surface: Close to NN155D. When opening and fully opened, outer surface: Distally, close to N57A; proximally, close to 157A.

*Sepals.*—To date, sepal development has not been observed on plants of the new *Aechmea.*

*Primary or scape bracts.*—Quantity and arrangement: One subtending each lateral panicle. Length: About 12 cm. Width: About 3.5 cm. Shape: Lanceolate. Apex: Acuminate. Base: Truncate. Margin: Entire. Texture and luster, upper surface: Smooth, glabrous; moderately glossy. Texture and luster, lower surface: Smooth, glabrous; densely covered with trichomes; slightly glossy. Color, upper surface: Close to 58B to 58C. Color, lower surface: Close to between N57B and 58B.

*Flower bracts.*—Quantity and arrangement: One per flower; subtending and closely appressed to the flower. Length: About 1.4 cm. Width, flattened: About 1.3 cm. Shape: Broadly ovate. Apex: Acute. Base: Truncate. Margin: Entire. Texture and luster, upper surface: Smooth, glabrous, waxy; glossy. Texture and luster, lower surface: Smooth, glabrous, waxy; densely covered with trichomes; moderately glossy. Color, upper surface: Close to 58D. Color, lower surface: Close to between N57A and 58A.

*Scapes.*—Length, primary, to base of inflorescence: About 48 cm. Diameter, primary: About 1.5 cm. Length, laterals: About 6 cm. Diameter, laterals: About 5 mm. Strength, primary and laterals: Strong. Aspect, primary: Upright. Aspect, laterals: Horizontal to slightly curving upright. Texture and luster, primary and laterals: Smooth, glabrous; densely covered with trichomes; slightly glossy. Color, primary and laterals: Close to N57A.

*Reproductive organs.*—Stamens: Quantity per flower: Six. Filament length: About 1 cm. Filament color: Close to 162A to 162B. Anther length: About 1 mm. Anther shape: Oblong. Anther color: Close to 162C. Pollen: None observed. Pistils: Quantity per flower: One. Pistil length: About 1.7 cm. Style length: About 1 cm. Style color: Close to 163C. Stigma shape: Ovoid. Stigma color: Close to N163D. Ovary color: Close to 157A.

*Seeds.*—To date, seed production has not been observed on plants of the new *Aechmea.*

Temperature tolerance: Plants of the new *Aechmea* have been observed to tolerate temperatures ranging from about 4° C. to about 36° C.

Pathogen & pest resistance: Plants of the new *Aechmea* have been observed to exhibit some resistance to *Phytophthora* and *Exserohelium*. Plants of the new *Aechmea* not been observed to be resistant to pests and other pathogens common to *Aechmea* plants.

It is claimed:

1. A new and distinct *Aechmea* plant named 'Pink Tango' as illustrated and described.

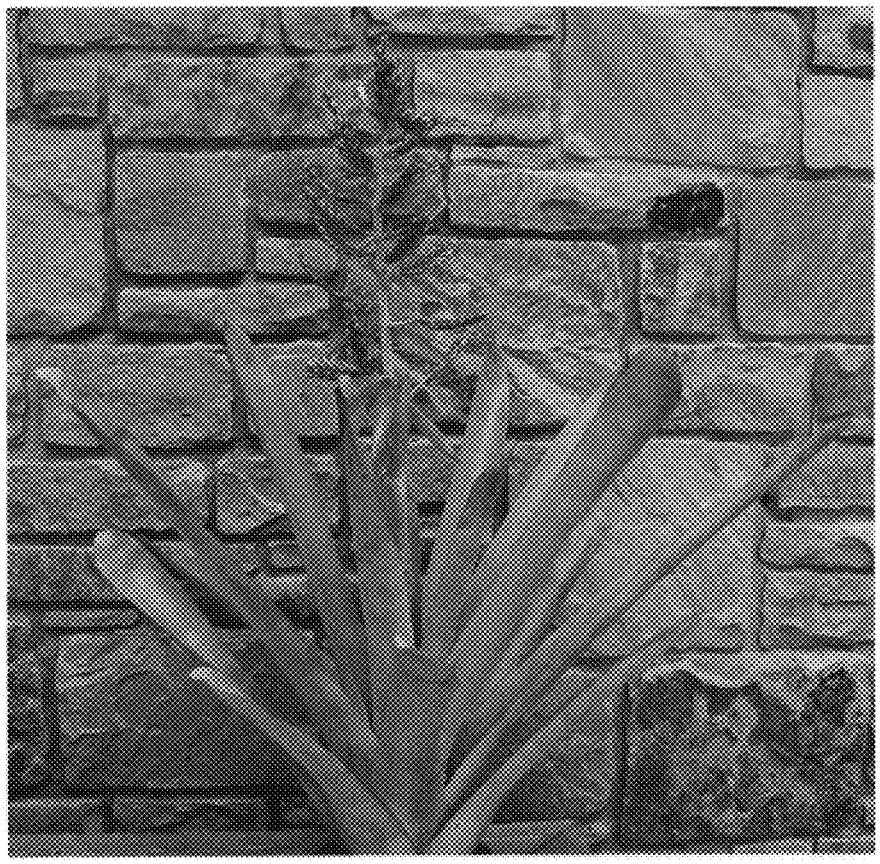

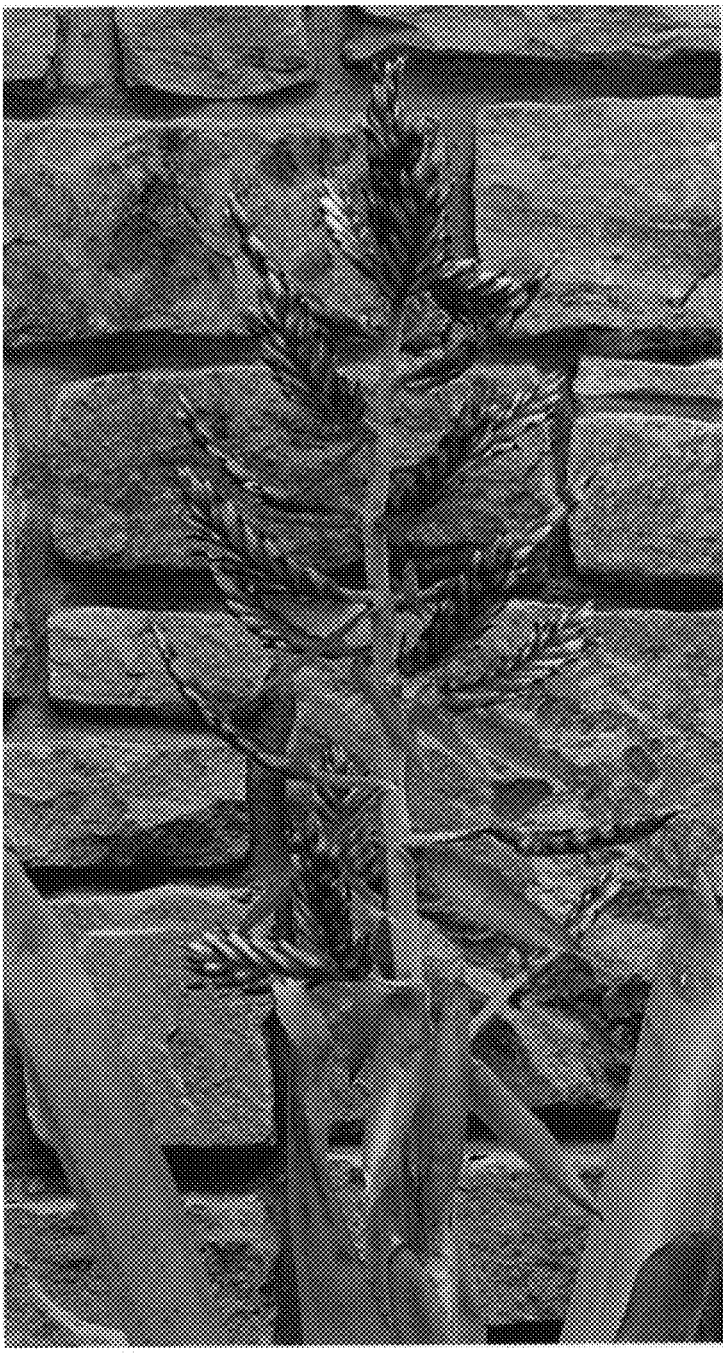

* * * * *